(12) United States Patent
Weber et al.

(10) Patent No.: US 11,737,720 B2
(45) Date of Patent: Aug. 29, 2023

(54) SYSTEM AND METHOD FOR PROVIDING IMAGING PARAMETERS

(71) Applicant: DÜRR DENTAL SE, Bietigheim-Bissingen (DE)

(72) Inventors: Michael Weber, Burgstetten (DE); Bernd Philipps, Untergruppenbach (DE)

(73) Assignee: DÜRR DENTAL SE

( * ) Notice: Subject to any disclaimer, the term of this patent is extended or adjusted under 35 U.S.C. 154(b) by 656 days.

(21) Appl. No.: 16/332,456

(22) PCT Filed: Sep. 12, 2017

(86) PCT No.: PCT/EP2017/072840
§ 371 (c)(1),
(2) Date: Mar. 12, 2019

(87) PCT Pub. No.: WO2018/046750
PCT Pub. Date: Mar. 15, 2018

(65) Prior Publication Data
US 2021/0286094 A1    Sep. 16, 2021

(30) Foreign Application Priority Data
Sep. 12, 2016 (DE) ............. 10 2016 117 051.8

(51) Int. Cl.
*H04N 5/32* (2023.01)
*A61B 6/00* (2006.01)
(Continued)

(52) U.S. Cl.
CPC ............ *A61B 6/5294* (2013.01); *A61B 6/145* (2013.01); *A61B 6/425* (2013.01); *A61B 6/4216* (2013.01);
(Continued)

(58) Field of Classification Search
CPC ....... A61B 6/563; G01T 1/2012; H04N 7/183
See application file for complete search history.

(56) References Cited

U.S. PATENT DOCUMENTS 4,672,184 A  6/1987 Fujiwara et al.
5,027,380 A  6/1991 Nishiki
(Continued)

FOREIGN PATENT DOCUMENTS

CN  102 422 222  4/2012
CN  103 988 265  8/2014
(Continued)

OTHER PUBLICATIONS

Unpublished U.S. Appl. No. 16/332,445, filed Mar. 12, 2019.
(Continued)

*Primary Examiner* — David P Porta
*Assistant Examiner* — Fani Polyzos Boosalis
(74) *Attorney, Agent, or Firm* — Schroeder Intellectual Property Law Group, LLC

(57) ABSTRACT

A system that comprises an X-ray imaging device for capturing an X-ray image on an imaging film, and a device for reading out said imaging film. The imaging film includes an optically readable marking, and the X-ray imaging device and/or the readout device includes a device for reading information stored on the data carrier, the data device being designed to register the optically readable marking using said readout device. A method for providing information for a readout device is also disclosed.

8 Claims, 4 Drawing Sheets

(51) Int. Cl.
*G01T 1/20* (2006.01)
*A61B 6/14* (2006.01)
*G06K 19/06* (2006.01)

(52) U.S. Cl.
CPC .......... *A61B 6/4452* (2013.01); *A61B 6/4458* (2013.01); *A61B 6/4494* (2013.01); *A61B 6/52* (2013.01); *G01T 1/2012* (2013.01); *G01T 1/2014* (2013.01); *G06K 19/06028* (2013.01); *H04N 5/32* (2013.01); *A61B 6/14* (2013.01)

(56) References Cited

U.S. PATENT DOCUMENTS

| | | | |
|---|---|---|---|
| 5,148,464 A | 9/1992 | Metoki | |
| 5,195,123 A | 3/1993 | Clement | |
| 5,231,656 A | 7/1993 | Sakuma et al. | |
| 5,264,684 A | 11/1993 | Weil | |
| 5,288,977 A | 2/1994 | Amendolia et al. | |
| 5,376,806 A | 12/1994 | Hejazi | |
| 5,377,253 A | 12/1994 | Ifuku | |
| 5,596,202 A | 1/1997 | Arakawa | |
| 5,757,021 A | 5/1998 | Dewaele | |
| 6,381,416 B2 | 4/2002 | Manico et al. | |
| 6,710,891 B1 | 3/2004 | Vraa et al. | |
| 7,319,396 B2 | 1/2008 | Homanfar et al. | |
| 7,355,195 B2 | 4/2008 | Ivo | |
| 7,397,058 B2 | 7/2008 | Struble et al. | |
| 7,561,668 B2 | 7/2009 | Ohta et al. | |
| 7,620,230 B2 | 11/2009 | Haug et al. | |
| 7,628,537 B2 | 12/2009 | Schulze-Ganzlin | |
| 7,896,229 B2 | 3/2011 | Crucs et al. | |
| 8,833,647 B2 | 9/2014 | Berger et al. | |
| 8,866,096 B2 | 10/2014 | Eguchi | |
| 9,245,161 B2 * | 1/2016 | Berger ................. | A61B 6/4494 |
| 9,351,690 B2 | 5/2016 | Nachaliel | |
| 9,384,864 B2 | 7/2016 | Nelson et al. | |
| 9,626,613 B2 | 4/2017 | Berger et al. | |
| 9,678,420 B2 | 6/2017 | Taskinen et al. | |
| 9,955,933 B2 | 5/2018 | Taskinen et al. | |
| 10,139,497 B2 | 11/2018 | Philipps et al. | |
| 10,393,889 B2 | 8/2019 | Philipps et al. | |
| 10,591,615 B2 | 3/2020 | Philipps et al. | |
| 10,722,198 B2 | 7/2020 | Thibaut et al. | |
| 10,835,195 B2 | 11/2020 | Taskinen et al. | |
| 2005/0133730 A1 | 6/2005 | Haug et al. | |
| 2005/0134936 A1 | 6/2005 | Haug et al. | |
| 2009/0212107 A1 | 8/2009 | Crucs et al. | |
| 2010/0104065 A1 | 4/2010 | Eguchi | |
| 2010/0266187 A1 | 10/2010 | Crucs | |
| 2012/0001737 A1 | 1/2012 | Berger et al. | |
| 2012/0019369 A1 | 1/2012 | Taskinen et al. | |
| 2012/0181437 A1 | 7/2012 | Nelson et al. | |
| 2014/0049380 A1 | 2/2014 | Berger et al. | |
| 2014/0252252 A1 | 9/2014 | Philipps et al. | |
| 2015/0324680 A1 * | 11/2015 | Berger ................. | A61B 6/145 235/375 |
| 2017/0238891 A1 | 8/2017 | Taskinen et al. | |
| 2018/0214102 A1 | 8/2018 | Taskinen et al. | |
| 2018/0354083 A1 | 12/2018 | Thorwarth | |
| 2019/0049598 A1 | 2/2019 | Philipps et al. | |
| 2019/0339401 A1 | 11/2019 | Philipps et al. | |
| 2021/0085269 A1 | 3/2021 | Taskinen et al. | |
| 2021/0282729 A1 | 9/2021 | Weber et al. | |

FOREIGN PATENT DOCUMENTS

| | | | |
|---|---|---|---|
| EP | 0 908 762 | 4/1999 | |
| EP | 1 544 673 | 6/2005 | |
| EP | 1544672 A1 * | 6/2005 | .......... G01T 1/2016 |
| EP | 2 386 904 | 11/2011 | |
| JP | S58-72041 | 4/1983 | |
| JP | S58-83937 | 5/1983 | |
| JP | S61-25530 | 2/1986 | |
| JP | H06-202254 | 7/1994 | |
| JP | H07-92584 | 4/1995 | |
| JP | H08-87085 A | 4/1996 | |
| JP | H11-202433 | 7/1999 | |
| JP | 2000-284116 A | 10/2000 | |
| JP | 2003-210446 | 7/2003 | |
| JP | 2006-048072 | 2/2006 | |
| JP | 2006-065347 | 3/2006 | |
| JP | 2011-043977 | 3/2011 | |
| JP | 2011-251119 | 12/2011 | |
| JP | 2012-521238 A | 9/2012 | |
| JP | 2015-213754 | 12/2015 | |
| WO | 2007/141985 | 12/2007 | |
| WO | 2010/109064 | 9/2010 | |
| WO | 2017/089224 | 6/2017 | |

OTHER PUBLICATIONS

Directives, Official Journal of the European Union, dated Dec. 5, 2013, 73 pages.
Opposition filing in European Patent Application No. 17776950.2 dated Nov. 23, 2021, 30 pages.
Office Action in Japanese Patent Application No. 2019-507337 dated Apr. 27, 2021, 2 pages.

* cited by examiner

SYSTEM AND METHOD FOR PROVIDING IMAGING PARAMETERS

RELATED APPLICATIONS

This application is a national phase of International Patent Application No. PCT/EP2017/072840 filed Sep. 12, 2017, which claims priority to German Patent Application No. 10 2016 117 051.8 filed Sep. 12, 2016—the contents of both of which are incorporated herein by reference.

FIELD OF THE INVENTION

The invention relates to a system comprising an x-ray recording device for recording an x-ray image on a phosphor plate and a readout device for the phosphor plate.

BACKGROUND OF THE INVENTION

These days, such systems are used within the scope of x-ray technology, for example in dentistry, for recording x-ray images. For the purposes of storing the x-ray image, the phosphor plate comprises a phosphor material embedded in a transparent matrix. As a result, storage centers arise, which can be brought into excited metastable states by incident x-ray light. If such a phosphor plate is exposed in an x-ray apparatus, for example for recording a bitewing of a patient, a latent x-ray image in the form of excited and non-excited storage centers is contained by the phosphor plate.

For the purposes of reading the phosphor plate, the latter is scanned point-by-point by readout light in a readout device, for example a scanning device, as result of which the metastable states of the excited storage centers are brought into a state which relaxes under the emission of fluorescence light. This fluorescence light is captured with the aid of a detector unit, and so the x-ray image becomes visible by way of appropriate evaluation electronics.

Unambiguous tracing and assignment of the phosphor plates is extremely important in medicine. For this purpose, identification systems are used here—as is also the case in many other logistics sectors.

SUMMARY OF THE INVENTION

It is an object of the invention to specify an easily manageable, reliable and cost-effective system and method for providing information items for a readout device.

This object may be achieved by a system having an x-ray recording device for recording an x-ray image on a phosphor plate and a readout device for the phosphor plate, wherein the phosphor plate has an optically readable marking and the x-ray recording device and/or the readout device comprises a data device for reading information items stored on the data carrier, wherein the data device is designed to capture the optically readable marking by means of the readout device. This object may also be achieved by a phosphor plate designed to be stored in a light protection sleeve, wherein the phosphor plate has an optically readable marking, in particular a barcode or QR code, wherein the optically readable marking is attached in such a way that it is readable by a readout device that is designed to read an x-ray image. This object may also be achieved by a method for providing information items for a readout device where an exposure process of a phosphor plate is performed using an x-ray recording device, the phosphor plate is read by means of the readout device, and the data carrier is read by means of the readout device.

The system according to the invention comprises an x-ray recording device for recording an x-ray image on a phosphor plate and a readout device for the phosphor plate. According to the invention, provision is made for the phosphor plate to have an optically readable marking as a data carrier. Moreover, provision is made for the x-ray recording device and/or the readout device to comprise a data device for reading information items stored on the data carrier, wherein the data device is designed to capture the optically readable marking by means of the readout device. By way of example, the optically readable marking can be a barcode or a QR code. The two-fold use of the readout device can facilitate a particularly cost-effective and, at the same time, efficient readout of the information items stored on the data carrier. The readout device that is present in any case can be actuated by the data device in such a way that it is also possible to capture a readout of an optically capturable marking such as a barcode, a QR code or the like. Consequently, the system according to the invention renders it possible to gather appropriate information items from the data carrier for a recording of an x-ray image on the phosphor plate. By way of example, said information items can be recording parameters that should be used for the recording with the x-ray appliance. Moreover, the number of times the phosphor plate has been used can be captured by means of the information items to be read in order to be able to calculate or estimate probable wear of the phosphor plate.

In one embodiment of the system, provision can be made for the information items to represent an identification code that uniquely identifies the phosphor plate. Consequently, the phosphor plate can be unambiguously identified by reading the information items stored on the data carrier. This allows data captured differently, for example the generation and/or capture of wear data, to be linked in a phosphor-plate-related manner. Moreover, together with the unique identification, it is also possible, for example, to link data of the phosphor plate or of the x-ray image stored thereon, which data is linked therewith and stored differently. It is also possible to link additional information items stored on the data carrier, such as, for example, recording parameters, wear data or the like, to the unique identification.

In a development of the invention according to the invention, provision is made for the data device to be configured to transmit the read information items to the readout device. Consequently, the information items situated on the data carrier are available to the readout device for the phosphor plate, for example already prior to the readout process, and the readout of the phosphor plate can for example already be adapted to the recording parameters that were used when recording the x-ray image. By way of example, the recording parameters can be present as centrally stored data and can be identifiable by means of the read information items.

By way of example, the recording parameters can be a voltage, a current, an exposure time, a dose, a dose area product, an aperture value, data relating to a patient and/or data relating to an order. Storing the aforementioned recording parameters establishes a link between the aforementioned parameters and the x-ray image stored on the phosphor plate, and consequently allows the x-ray recording to be tracked.

The phosphor plate according to the invention has a light-sensitive layer, in particular for storing an x-ray image, and it is designed to be stored in a light protection sleeve.

According to the invention, provision is made for the phosphor plate to have an optically readable marking, in particular a barcode or QR code.

Consequently, this optically readable marking is attached to a location that is not readable during conventional handling of the phosphor plate since the phosphor plate is normally housed in a protective sleeve. However, attaching an optically readable marking provides the option of capturing the latter, for example when the phosphor plate is read. The light-sensitive layer is activated by means of a readout laser beam when the phosphor plate is read. Thus, the phosphor plate is situated outside of the light protection sleeve in this context and hence it is accessible for the capture of the optically readable marking. Preferably, readout can be performed directly using the readout light for the phosphor plate. Alternatively, it is also possible to use another light source, for example also with a wavelength that does not influence the readout process. By way of example, the marking that is readable optically can be an identification of the phosphor plate.

The method according to the invention for providing information items for a readout device includes the following steps: an exposure process of a phosphor plate is performed by means of an x-ray recording device such that an x-ray image arises on the phosphor plate. The phosphor plate is read by means of the readout device. The data carrier is read by means of the readout device. Here, the aforementioned sequence is not mandatory. Thus, recording parameters that should be used during an x-ray recording can be read from the data carrier prior to the exposure of the phosphor plate. Further, a marking of the phosphor plate that characterizes the phosphor plate can be read from the data carrier before or after the exposure.

Moreover, provision can be made for the step of reading the phosphor plate to take account of the readout result of the data carrier. By way of example, if the recording parameters with which the x-ray image was exposed onto the phosphor plate are considered when reading the phosphor plate, it may be possible to optimize the readout conditions for the phosphor plate in certain circumstances.

BRIEF DESCRIPTION OF THE DRAWINGS

The invention will now be explained in more detail with reference to the attached drawings. In the figures.

DETAILED DESCRIPTION OF THE INVENTION

Figure 1A:
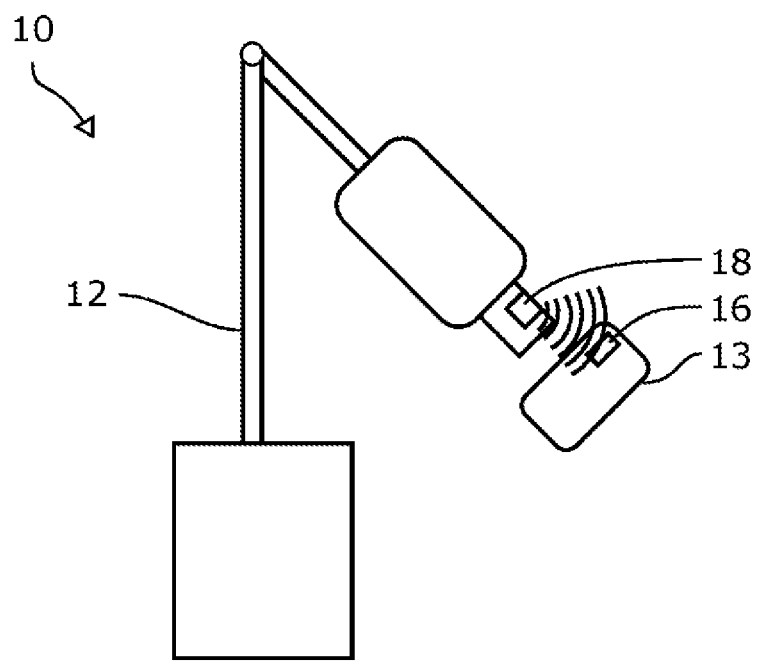
FIGS. 1A, 1B show schematic illustrations of parts of a system according to the invention.
Figure 1B:
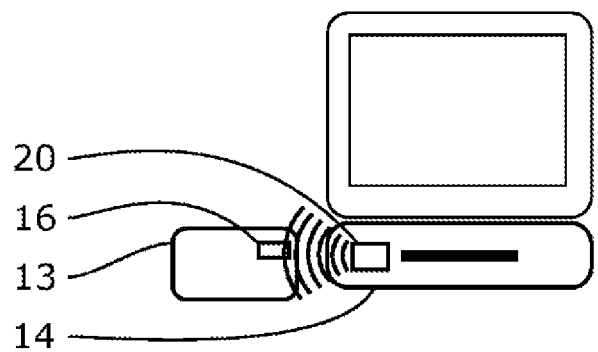

FIGS. 1A and 1B illustrate a system 10 for providing information items. The system 10 comprises an x-ray recording device 12 (FIG. 1A) for exposing a phosphor plate 13 with an x-ray image, as are used in dentistry, for example, and a readout device 14 for reading the x-ray image situated on the phosphor plate 13. For the purposes of recording an x-ray image, the phosphor plate 13 is usually arranged at a suitable position in the oral cavity of a patient by means of holding devices that are not illustrated here, and exposed by way of the x-ray recording device 12. For the exposure, recording parameters that are suitable for the respective recording situation should be set on the x-ray recording device 12. By way of example, these recording parameters comprise a voltage, a current, an exposure time, a dose, a dose area product and/or an aperture value, and hence these recording parameters determine the recording conditions. However, patient-specific or order-specific information items may also be contained in the recording parameters.

In addition to the actual x-ray-beam-sensitive structure, the phosphor plate 13 comprises an RFID transponder 16. By way of example, the RFID transponder 16 can be arranged on or in a lightproof protection sleeve that is usually provided. The RFID transponder 16 works together with a write/read device 18 on the x-ray recording device 12 and a read appliance 20 on the readout device 14. As an alternative or in addition thereto, the phosphor plate 13 can have an optically readable structure, such as a barcode, for example.

The write/read device 18 provided on the x-ray recording device 12 is designed to write some or all of the recording parameters onto the RFID transponder 13. To this end, the intended values set prior to the exposure process and/or measurement values captured during or after the exposure process, for example, can be captured as recording parameters and can be written onto the RFID transponder 16. Additionally, the write/read device 18 can also read information items situated on the RFID transponder. By way of example, information items relating to the patient, the order, the x-ray system and/or the overall system or similar information items can be stored on the RFID transponder 16, for example already when preparing the x-ray recording on the phosphor plate 13, said information items then being read by the x-ray recording device 12 and possibly being included in the configuration of the exposure process of the phosphor plate 13.

After the exposure has been implemented, the x-ray image situated on the phosphor plate 13 has to be read. The readout device 14 is provided to this end in the shown embodiment of the system 10. By way of example, the readout device 14 can be a scanning device, which activates the metastable states in the phosphor plate matrix by means of a guided laser beam and which thus facilitates a readout of the x-ray image. By way of example, the recording parameters contained in the RFID transponder 16 can be read by means of the reading appliance 20 provided on the readout device 14 already prior to the readout process of the phosphor plate 13, and can be used for the readout/scanning process where applicable. Knowledge about the recording parameters may simplify setting the readout process under certain circumstances.

The reading appliance 20 provided on the readout device 14 can also be embodied as a write/read device similar to the write/read device 18. Thus, information items still situated on the RFID transponder 16 after the readout of the phosphor plate 13 can be erased again. As an alternative or in addition thereto, some or all of the readout results can be written onto the RFID transponder 16 in turn and can thus be stored. It is also possible to store a note on the RFID transponder 16, which indicates that the phosphor plate 13 has already been read.

Figure 2A:
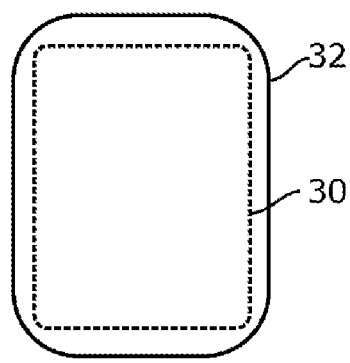
FIGS. 2A-D show schematic illustrations of various embodiments of a phosphor plate according to the invention.

FIGS. 2A-D show an embodiment of a phosphor plate 30. As shown in FIG. 2A, the phosphor plate 30 is inserted in a protection sleeve 32 during the handling thereof. The protection sleeve 32 serves as a mechanical protection for protecting the sensitive phosphor plate 30 from scratches and bending. At the same time, the protection sleeve 32 protects the phosphor plate 30 from an unwanted incidence of light, which would destroy the latent stored image situated on the phosphor plate 30 or which would undesirably expose a still unexposed phosphor plate. For readout purposes, the phosphor plate 30 should be removed from the protection sleeve in protective surroundings and scanned point-by-point or line-by-line using a readout light, as a result of which the metastable states of the excited storage centers, which store the x-ray image, relax and emit fluorescence light.

Figure 3:
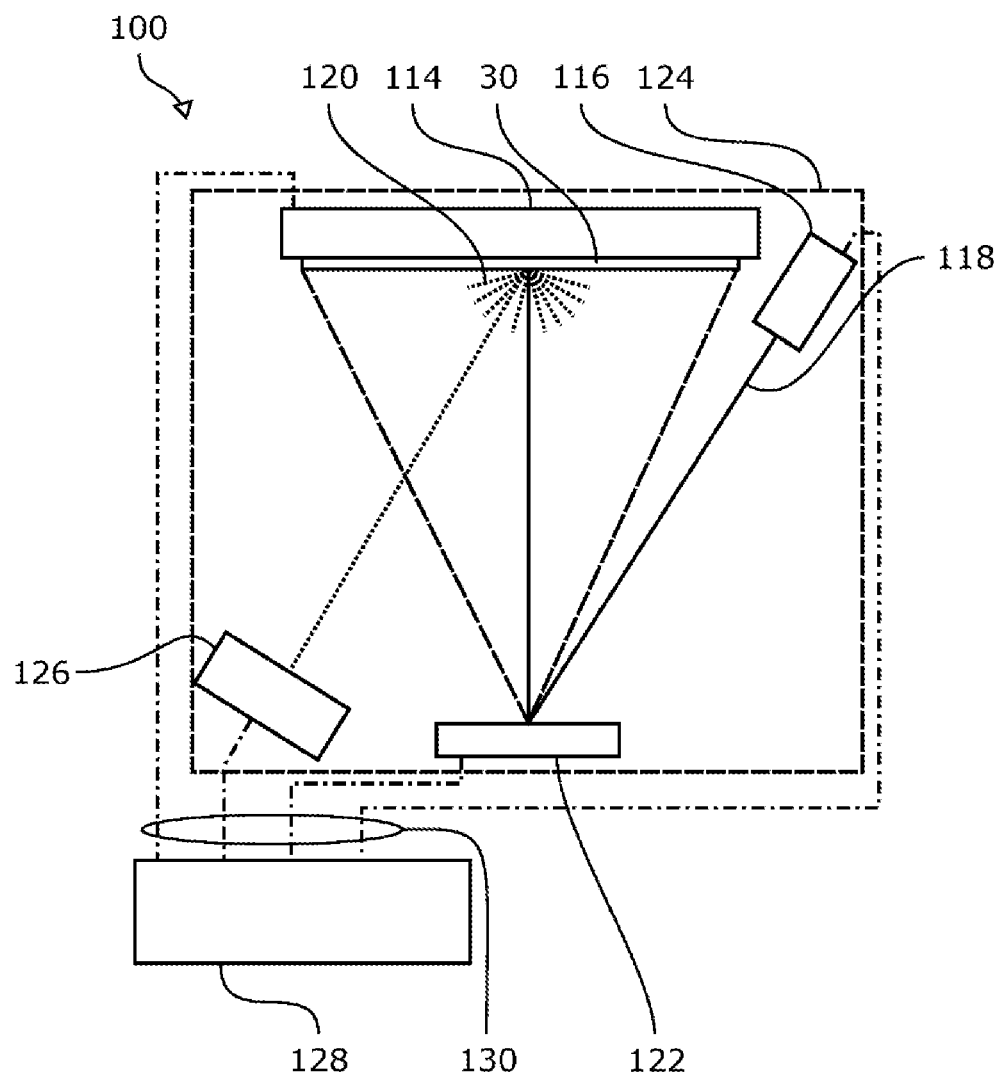
FIG. 3 shows a schematic illustration of an embodiment of a readout device.

FIG. 3 shows a scanning device 100 for reading such a phosphor plate 30, which carries a latent x-ray image in the form of metastable storage centers that were excited by x-ray radiation.

The scanning device 100 has a support device 114 for the phosphor plate 30. By way of example, the phosphor plate 30 can be fastened to the support device 114 with a negative pressure in such a way that the phosphor plate 30, which is generally flexible, presses closely against the support surface 114 in planar fashion.

The scanning device 100 further comprises a laser 116 as a readout light source, said laser producing a readout light beam 118 with a wavelength lying in the red spectrum, by means of which the metastable storage centers of the phosphor plate 30 can be excited to fluoresce. This fluorescence light 120 typically lies in the blue spectrum.

In the present embodiment of the scanning device 100, the laser 116 is arranged in such a way that it directs the readout light beam 118 onto a controllable deflection unit. The controllable deflection unit is embodied as a mirror 122 in the present case. However, other deflection units, such as optical units or the like, are conceivable in addition to mirrors. The mirror 122 can be embodied as a micromirror, in particular as a MEMS component and can thus facilitate a scanning of the surface of the phosphor plate 30 without relative movement, or with only little relative movement, between the mirror 122 and support device 114. As an alternative, the mirror 122 can also be provided in conventional fashion as a rotating mirror for a drum scanner. In this case, a relative movement between the support device 114 and the mirror 122 is realized by means of a transportation device (not imaged).

Further, the scanning device 100 may comprise a reflector 124, indicated by dashed lines in the drawing, said reflector surrounding the entire measurement space around the phosphor plate 30 in lightproof fashion such that the fluorescence light 120 emanating from the phosphor plate 30 is reflected to a photodetector 126. It is possible to provide suitable measures, such as dichroic filter material, for instance, to prevent scattered readout light 118 from reaching the photodetector 126.

For the purposes of controlling the readout process, the scanning device 100 comprises a control unit 128 which for example can also adopt evaluation or correction functions in addition to the control function. However, the control unit 128 itself or the evaluation and/or correction functions can also be implemented on a separate computer. The control unit 128 is connected to the support device 114, the detector 126, the laser 116 and the mirror 122 by means of lines 130.

For readout purposes, the control unit 128 actuates the laser 116 and the mirror 122 and sequentially scans the phosphor plate 30 point-by-point by means of the readout light beam 118. In the process, the intensity of the emitted fluorescence light 120 is captured with the aid of the photodetector 126 and prepared in the control unit 128 for output.

Figure 2B:
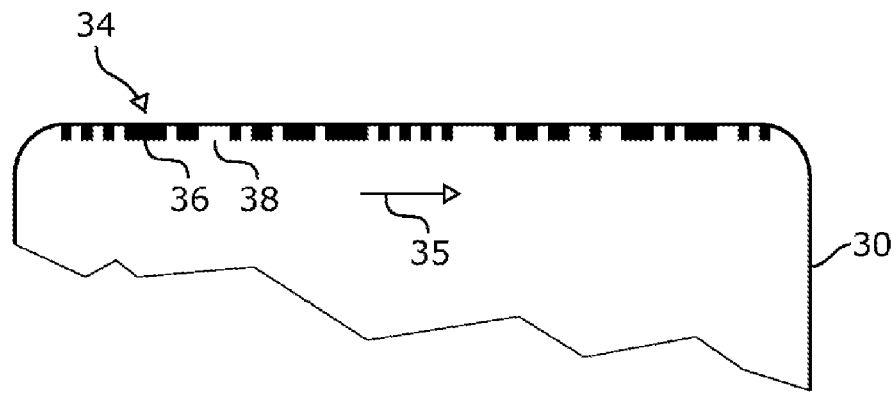
Figure 2C:
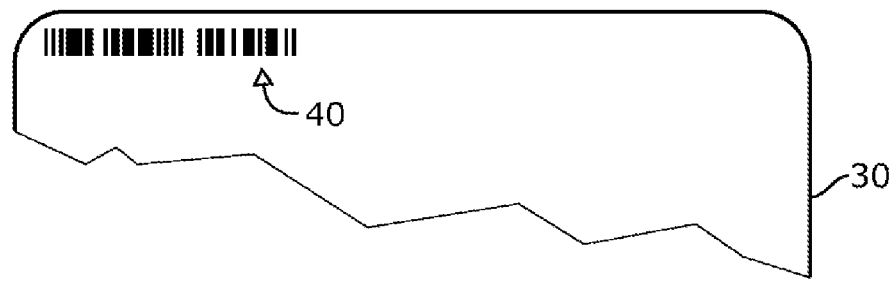
Figure 2D:
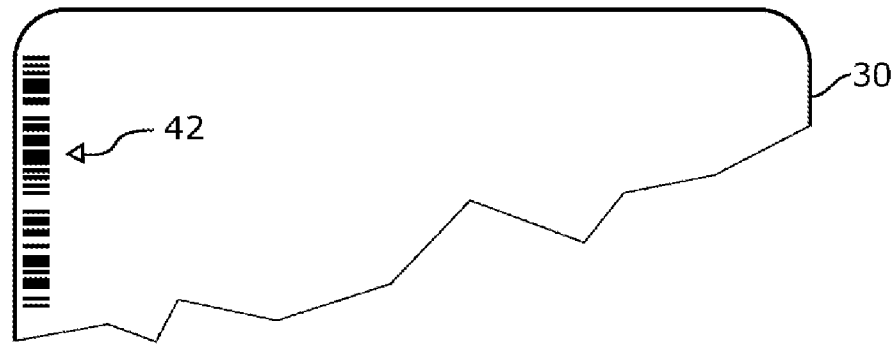

FIGS. 2B-D illustrate three different embodiments of a phosphor plate 30. The phosphor plate 30 illustrated in FIG. 2B has a barcode structure 34 on its upper edge, said barcode structure substantially covering the entire width of the phosphor plate 30 in the direction 35 of a scanning line. The barcode structure 34 is embodied in such a way that it has regions 36 with increased reflectivity for the readout light beam 118 and regions 38 with less reflectivity, for example normal reflectivity, when reading the phosphor plate, for example by means of a scanning device 100 in the scanning direction of the readout light beam 118. By way of example, the regions 36 with increased reflectivity can act as scattering regions. Consequently, the stray light arising from the barcode structure 34 during a line-by-line scan can be detected prior to a normal readout process when scanning the phosphor plate. Since a high spatial resolution is not important in this process, the stray light can be captured by a simple photodiode (not imaged), for example. As an alternative or in addition thereto, the photodetector 1126 present in any case can possibly assume this task in the case of the low required sensitivity.

FIGS. 2C and D show developments. In contrast to the barcode structure of FIG. 2B, the barcode structure 40 only covers part of the surface of the phosphor plate 30 in the scanning direction 35. In the development shown in FIG. 2D, a barcode structure 42 extends perpendicular to the line-by-line scanning direction 35 and consequently requires a detection of the arising stray light at the start of each scanning line.

The information items obtained by reading or capturing the barcode structures can serve, for example, to identify data such as recording parameters, for example, which are stored centrally. Consequently, an improved readout of the actual x-ray image can likewise be achieved by means of information items which are indirectly obtainable by way of the phosphor plate itself.

Figure 4:
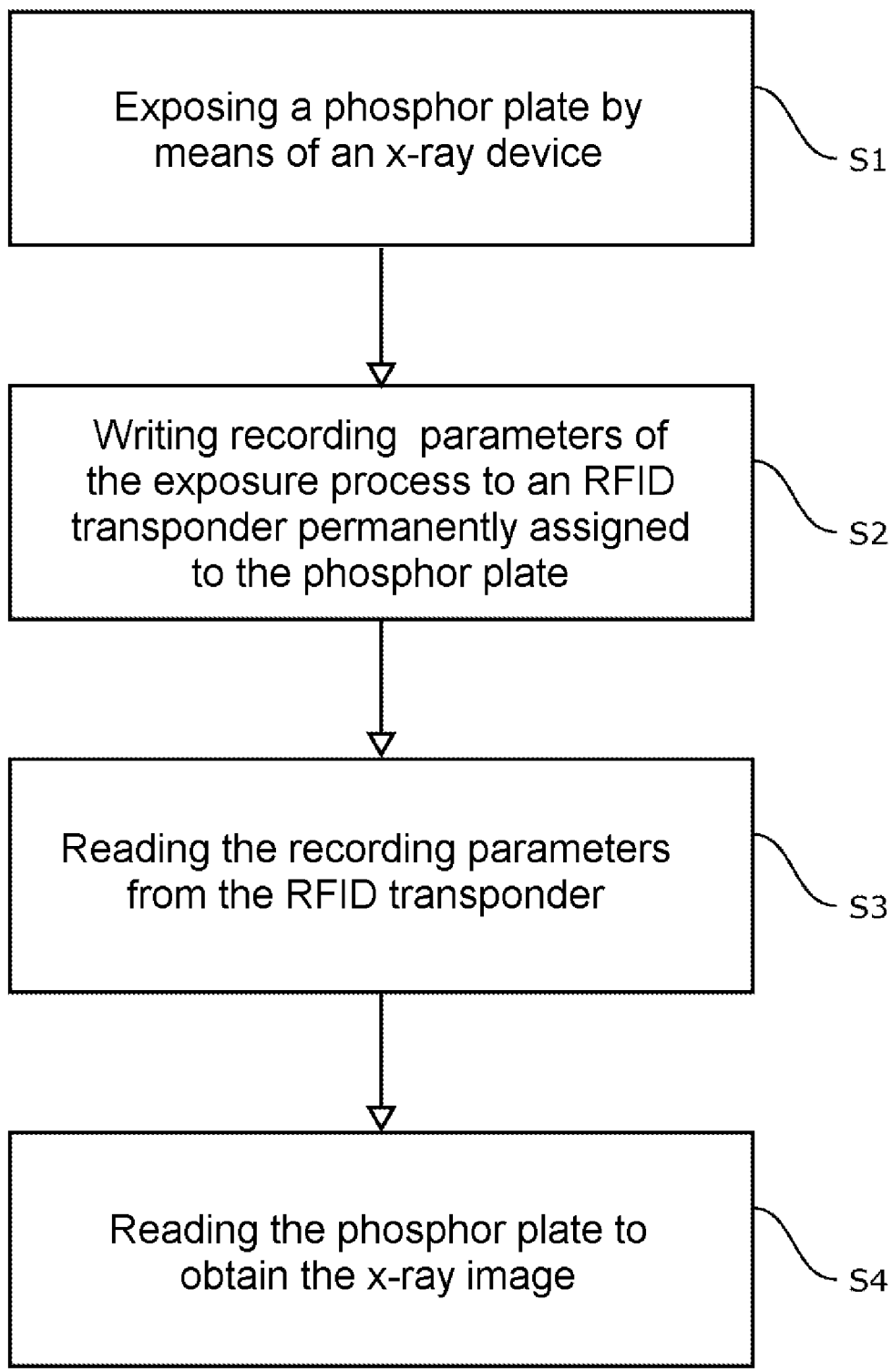
FIG. 4 shows a flowchart of a method according to the invention.

FIG. 4 describes an embodiment of a method for providing information items for a readout device. The method includes the following steps:

A phosphor plate is exposed by means of an x-ray device (S1). During the exposure process, an x-ray image is produced in the phosphor plate in latent fashion.

An RFID transponder permanently assigned to the phosphor plate is written to (S2) with recording parameters of the exposure process. The process of writing (S2) can already occur prior to the step of exposure (S1) if only intended values to be set should be saved on the RFID transponder. As an alternative or in addition thereto, the process of writing (S2) can take place during or after the exposure process (S1) and, as an alternative or in addition thereto, measurement values captured during the exposure process (S1) can also be stored on the RFID transponder. For the purposes of writing to the RFID transponder, the phosphor plate can remain in the x-ray device or can already have been removed from the x-ray device.

The recording parameters situated on the RFID transponder are read (S3). The phosphor plate can be transported to a readout device, so as to read the recording parameters there, after the end of the exposure process (S1) and the writing to the RFID transponder (S2).

The x-ray image situated on the phosphor plate is read (S4) by means of a suitable readout device. Here, this can be a scanning device, for example, which activates the latent x-ray image by means of a laser and thus facilitates a readout. The steps of reading the recording parameters (S3) and of reading the phosphor plate (S4) can be implemented independently of one another. However, provision can also be made for the recording parameters to be read (S3) from the RFID transponder prior to reading the phosphor plate (S4) in order to obtain deductions about suitable settings for the readout of the phosphor plate from the recording parameters.

What is claimed is:

1. A system comprising:
an x-ray recording device for recording an x-ray image on a phosphor plate and
a readout device for the phosphor plate,
wherein
the phosphor plate has a data carrier comprising an optically readable marking and the readout device comprises a data device for reading information items stored on the data carrier, wherein the data device is designed to capture the optically readable marking by means of the readout device.

2. The system as claimed in claim 1, wherein the information items represent an identification code that uniquely identifies the phosphor plate.

3. The system as claimed in claim 1, wherein the data device is configured to transmit the read information items to the readout device.

4. The system as claimed in claim 1, wherein the optically readable marking is a barcode or a QR code.

5. A phosphor plate having a light-sensitive layer and designed to be stored in a light protection sleeve, comprising:
an optically readable marking, wherein
the optically readable marking is attached in such a way that it is readable by a readout device that is designed to read an x-ray image.

6. The phosphor plate as claimed in claim 5, wherein the optically readable marking is a barcode or a QR code.

7. A method for providing information items for a readout device, comprising the steps of:
performing an exposure process of a phosphor plate using an x-ray recording device;
reading the phosphor plate by means of a readout device; and
reading a data carrier comprising an optically readable marking by means of the readout device.

8. The method as claimed in claim 7, wherein the step of reading the phosphor plate takes account of the readout result of the data carrier.

* * * * *